United States Patent [19]

Nicol et al.

[11] 4,361,052

[45] Nov. 30, 1982

[54] SAMPLING OF GRANULAR MATERIAL FOR ANALYSIS

[75] Inventors: Robert W. Nicol, Kenmore; Martin Gottschall, Jindalee; Geoffrey Lyman, Taringa, all of Australia

[73] Assignee: The University Of Queensland, St. Lucia, Australia

[21] Appl. No.: 210,346

[22] Filed: Nov. 25, 1980

[30] Foreign Application Priority Data

Nov. 26, 1979 [AU] Australia .............................. PE1482

[51] Int. Cl.³ ............................................ G01N 1/00
[52] U.S. Cl. ................................... 73/863; 73/32 A; 73/73
[58] Field of Search ..................... 73/32 R, 32 A, 863; 250/277, 434, 438; 222/196, 200, 201

[56] References Cited

U.S. PATENT DOCUMENTS 4,019,547 4/1977 Ross ..................................... 222/196

FOREIGN PATENT DOCUMENTS 1173346 12/1969 United Kingdom .
1175356 12/1969 United Kingdom .
1196625 7/1970 United Kingdom .
1336861 11/1973 United Kingdom .
1413350 11/1975 United Kingdom .

Primary Examiner—S. Clement Swisher
Attorney, Agent, or Firm—Schwartz, Jeffery, Schwaab, Mack, Blumenthal & Koch

[57] ABSTRACT

A method of and apparatus for sampling granular material where a substantially vertical sampling tube is subjected to axial, and/or rotational oscillations to reduce the vertical vector component of the friction force between the granular material and the tube to be substantially equal to the weight of an elemental disc of the material in the sampling tube. The acceleration force on the disc is substantially zero and the material has no pressure gradient or bulk density gradient.

13 Claims, 6 Drawing Figures

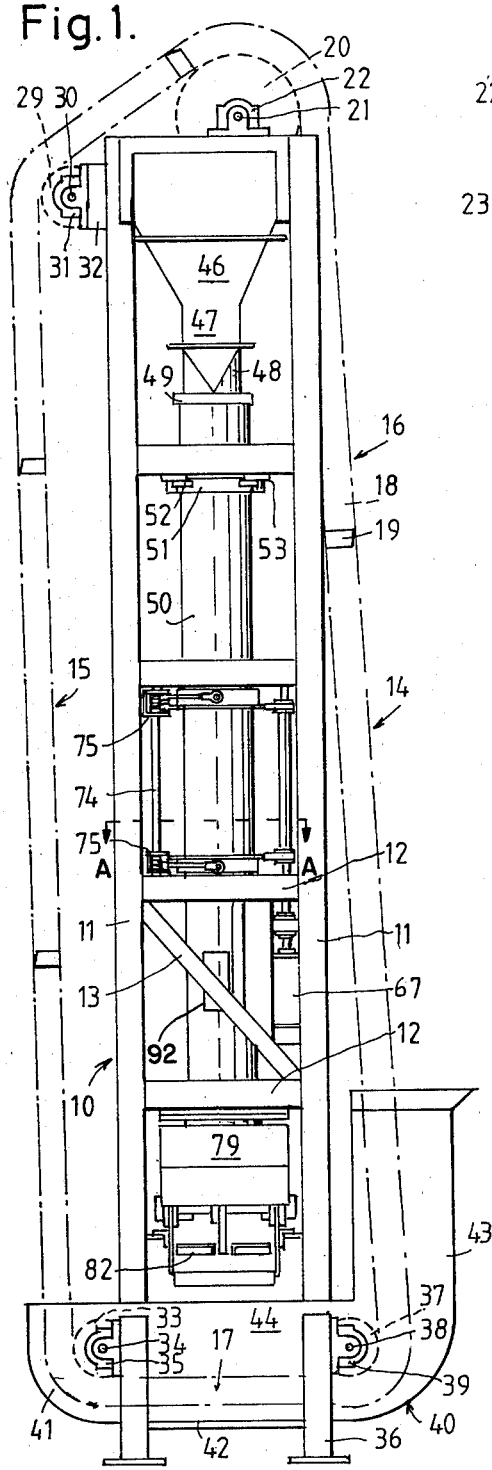
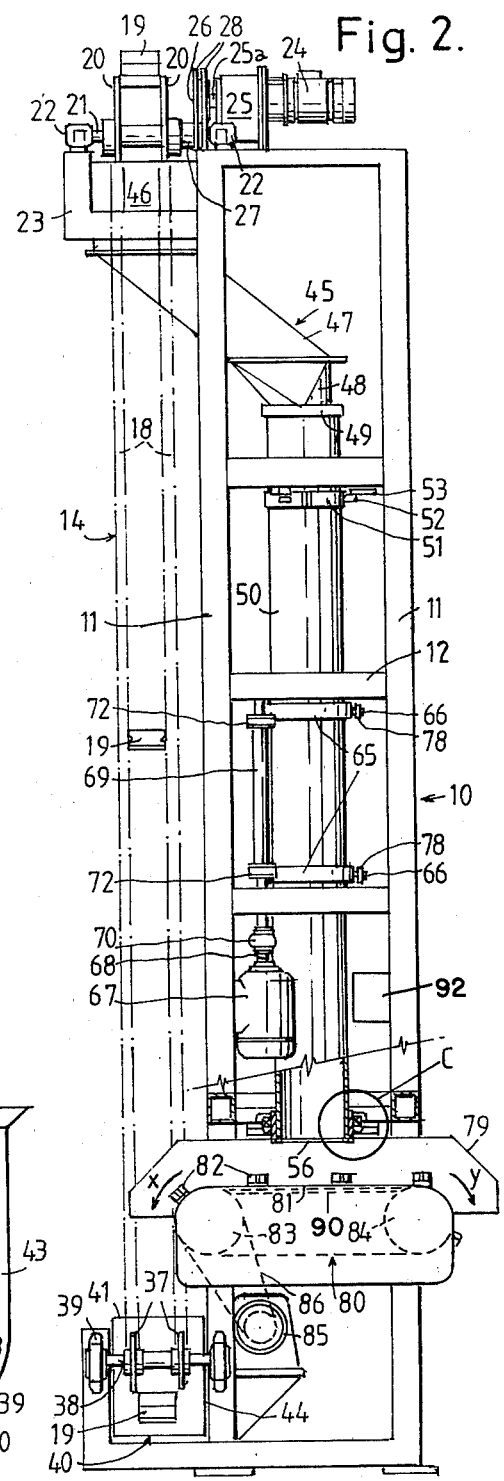
Fig. 1.
Fig. 2.

SAMPLING OF GRANULAR MATERIAL FOR ANALYSIS

BACKGROUND OF THE INVENTION (1) Field of the Invention

This invention relates to a method of and apparatus for sampling granular materials for analysis. The method and apparatus may also be applied to constant mass flow feeding of granular materials.

(2) Description of the Prior Art

It is desirable to analyse granular materials, e.g. coal, so as to obtain relevant parameters of the characteristics of the materials such as bulk density, moisture content, ash content and/or elemental composition.

While the techniques of analysis are well-known and accepted, the problem has been, and still is, to convey the granular material past the analysis station(s) without altering or changing any of these parameters.

One method of sampling coal for analysis employs a closed screw conveyor with a sampling tube of substantially constant cross-section. The coal is forced through the sampling tube and is compacted therein with the object of achieving approximately constant bulk density of the coal throughout the length of the tube.

Suitable analysis equipment is utilized to determine one or more of the parameters of the coal, e.g. ash content. This method has a number of serious disadvantages. Firstly, the length of the sampling tube is limited and not suitable to more general methods of coal analysis and to achieving compaction of the coal to approximately constant bulk density. High power consumption is required to drive the coal through the sampling tube and the high loads placed on the coal in directions transverse to the direction of motion of the coal can result in mechanical failure of the sampling tube. Finally, undesirable crushing of the coal is obtained due to its low inherent strength or impact resistance.

BRIEF SUMMARY OF THE INVENTION

It is therefore, an object of the present invention to provide a method for sampling granular material, such as coal, for analysis which alleviates one or more of the disadvantages of the prior art method described above.

It is a further object of the present invention to provide an apparatus for carrying out the method.

It is a preferred object to enable the adaption of the method and apparatus to the constant mass flow feeding of granular material.

It is a further preferred object of the present invention to reduce the vector component of the frictional force in the direction of flow applied to an elemental disc of material in the bulk moving along the sampling tube to be substantially equal to the weight of that elemental disc so that the pressure gradient or bulk density gradient across that disc is substantially zero.

It is a still further preferred object to provide alternative ways of effecting the method.

Other preferred objects of the present invention will become apparent to the skilled addressee from the following description.

In one aspect, the present invention provides a method of conveying granular material through a sampling tube for analysis, including the steps of:

(i) feeding granular material to the sampling tube;

(ii) subjecting the sampling tube to oscillation to reduce the frictional force between the granular material and the wall of the sampling tube to enable the granular material to pass through the tube with substantially no pressure gradient or bulk density gradient; and (iii) discharging the granular material from the sampling tube.

In a second aspect, the present invention provides an apparatus for conveying granular material through a sampling tube for analysis including:

a sampling tube having an inlet and an outlet;

means to support the sampling tube for oscillating movement;

means to feed granular material to the inlet of the sampling tube;

means for oscillating the sampling tube to reduce the frictional force between the granular material and the wall of the tube to enable the granular material to pass through the sampling tube with substantially no pressure gradient or bulk density gradient; and means for discharging the granular material from the outlet of the sampling tube.

The sampling tube may be relatively long, with a high length to diameter ratio. Preferably the sampling tube has a constant cross-section.

The granular material may be fed into the inlet of the sampling tube by any suitable means, e.g. hopper, chute or conveyor or a combination of these.

Preferably the sampling tube is substantially vertical, supported in a support frame, and the granulated material passes down the sampling tube under the influence of gravitational forces.

In step (ii) the sampling tube may be oscillated axially, rotationally or a combination of both, e.g. helically, and the frequency and/or amplitude of the oscillations may be fixed or selectively variable. Preferably the velocity and/or amplitude of the oscillations of the sampling tube are greater (more preferably, much greater) than the respective velocity and amplitude of the granular material in the sampling tube due to the inertia of the granular material.

Axial oscillation of the tube may be accomplished by suitable mechanical, pneumatic, electrical or hydraulic means or a combination of one or more of these. Suitable mechanical means include mechanical leverage systems or cam- or eccentric-operated means, while suitable pneumatic or hydraulic means include ram assemblies, and electrical means include solenoids or field coils.

Rotational oscillation may also be provided by similar means. One suitable mechanical means includes an eccentric drive coupled to a connecting rod attached to the sampling tube.

Helical oscillation may be provided by a combination of the above means.

Preferaby a pile of granular material closes the outlet of the sampling tube and granular material is removed from the pile by suitable conveying means, e.g. a belt-, cleat and chain-, rotary, screw- or vibrating conveyor. Preferably a constant mass flow of granular material is removed from the pile.

The analysis of the granular material passing through the sampling tube may be carried out by any suitable analysis technique and apparatus appropriate for the granular materials and parameters to be determined. For example, in determining the ash content of coal, the radio-isotope transmission or scatter and/or neutron capture and analysis techniques disclosed in U.S. Pat. No. 4,090,074 (J. S. Watt and V. L. Gravitis—assigned to the Australian Atomic Energy Commission) is of special interest.

BRIEF DESCRIPTION OF THE SEVERAL VIEWS OF THE DRAWINGS

To enable the invention to be fully understood, a preferred embodiment will now be described with reference to the accompanying drawings in which:

FIG. 1 is a front view of the sampling apparatus

FIG. 2 is a partly sectioned side view of the sampling apparatus of FIG. 1;

DETAILED DESCRIPTION OF THE PREFERRED EMBODIMENT

Figure 3:
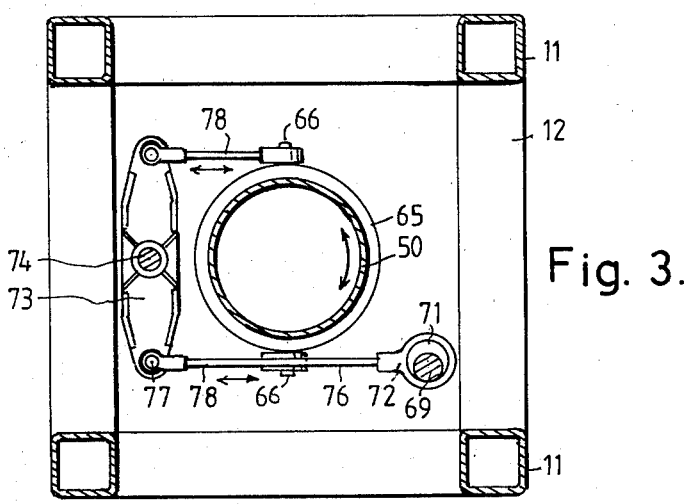
FIG. 3 is a sectional plan view taken on line A—A of FIG. 1.

The apparatus has a vertical frame 10 (rectangular in plan) comprising corner uprights 11, crossbeams 12 and braces 13. Portions of the frame 10 have been omitted for clarity.

A continuous bucket conveyor 14 has a forward run 15, return run 16 and a loading run 17. The conveyor 14 has a pair of parallel chains 18 which are interconnected at spaced intervals by open-mouthed buckets 19. The chains 18 pass over a pair of drive sprockets 20 fixed on a common shaft 21 journalled in suitable bearings 22 on a head frame 23 at the top of the frame 10.

An electric motor 24 is connected to the input shaft of a gearbox 25 and a double row sprocket 26 on the output shaft 25a of the gearbox is connected to a corresponding sprocket 27 on the shaft 21 via a pair of endless chains 28.

On the forward run 15 of the conveyor 14, the endless chains 18 pass over a pair of spaced guide sprockets 29 fixed on a shaft 30. The shaft 30 is journalled in bearings 31 mounted on a support frame 32 extending to one side of the head frame 23.

A pair of forward idler sprockets 33 are fixed on a shaft 34 journalled on bearings 35 on a tail frame 36 adjacent the base of the frame 10. A similar pair of return idler sprockets 37 are fixed on shaft 38 journalled in bearings 39 on the tail frame 36.

Between the forward and return idler sprockets 33, 37, the conveyor 14 follows a substantially horizontal path in its loading run 17 through an open-mouthed loading hopper 40 at the base of the frame 10.

The hopper 40 has a forward end wall 41 leading into a floor 42 and then to a rearward end wall 43 which is taller than the front end wall 41. The hopper 40 has side walls 44 which are substantially L-shaped in side view.

The conveyor 14 undergoes its substantially vertical return run 16 between the return idler sprockets 37 and the drive sprockets 20, the buckets 19 being filled with the granular material, e.g. coal, to be sampled.

When the buckets 19 pass over the drive sprockets 20, they are partially inverted and the granular material is tipped into a feed chute 45. The feed chute has an open-mouthed hopper 46 (with inclined walls) which receives the granular material. An inclined transfer chute 47 connected to the hopper 46 conveys the granular material under gravity to a substantially frusto-conical discharge chute 48 which has its mouth connected to the inlet 49 of the sampling tube 50.

The sampling tube 50 (formed of ABS plastic) is substantially vertical and mounted for rotational oscillation about a substantially vertical axis.

A metal clamping ring 51 is fixed to the tube 50 adjacent the inlet 49 and three cam-follower type rollers 52 (carried on support brackets 53) are equally spaced around the tube 50 and engage the clamping ring 51 to centre the tube.

Figure 4:
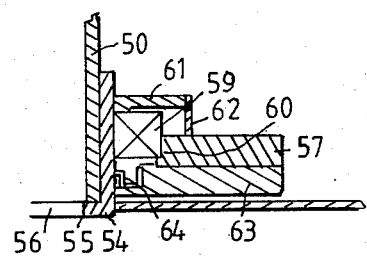
FIG. 4 is an enlarged view of detail "C" on FIG. 2.

Referring to FIG. 4, a base support ring 54, with an inner peripheral flange 55, is fitted to the outlet 56 of the sampling tube 50. A bearing support ring 57 is provided coaxially with the tube 50 and is supported on the frame 10 via suitable brackets 58. A thrust bearing 59 has its inner race fixed to the base support ring 54 and its outer race supported in an abutment 60 formed in the inner face of the bearing support ring 57.

A peripheral cover flange 61 is fixed to the base support ring 54 and provided with a flexible seal 62 which engages the upper face of the bearing support ring 57. An annular seal 63 is fixed to the underside of the bearing support ring 57 and has a flexible lip 64 which engages the base support ring 54. In this manner, the thrust bearing 59 is sealed from moisture and dust.

A pair of spaced drive rings 65 are clamped to the sampling tube 50 intermediate its length. A pair of diametrically opposed stub axles 66 extend radially from each ring 65.

An electric motor 67 is mounted on the frame 10 with its output shaft 68 connected to a vertical drive shaft 69 via a suitable flexible assembly 70, the drive shaft 69 being rotatably journalled in bearings (not shown) on the frame 10. A pair of spaced eccentric lobes 71 are fixed on the shaft 69.

A bearing eyelet 72 is journalled on each lobe 71 and is connected to one end of a rocker arm 73, (journalled on a vertical shaft 74 and supported by brackets 75) via a connecting link 76 which engages pivot pin 77 on the rocker arm 73.

Drive links 78 connect the respective ends of the rocker arm 73 to the adjacent stub axles 66 on sampling tube 50.

As motor 67 rotates the drive shaft 69, the eccentric lobes 71 cause the connecting links 76 to undergo a substantially reciprocating motion, causing the rocker arm 73 to oscillate about the axis of vertical shaft 74 and sampling tube 50 to rotatably oscillate about its vertical axis.

A discharge hood 79 is mounted on the frame 10 to surround outlet 56 of the sampling tube 50.

A tray 90 is provided under the top rim of a reversible discharge conveyor 80 to support the granular material (under the hood 79) discharged from the outlet 56 of the sampling tube 50.

The conveyor 80 has one endless chain 81 provided with a series of spaced transverse cleats 82. The chain 81 passes around a drive sprocket 83 and an idler sprocket 84, the drive sprockets 83 being driven by a reversible electric motor 85 via a suitable belt-and-pulley transmission 86.

The conveyor 80 may be operated in the direction X to return the discharged material to hopper 40 or in the direction of Y for discharge from the sampling apparatus.

In operation, the bucket conveyor 14 and discharge conveyor 80 are set in operation and the sampling tube 50 is driven via the rocker arm 73 for rotational oscillation at a frequency of, e.g. 25 Hertz.

Coal is picked up from the hopper 40, is discharged into the feed chute 45 and enters the inlet 49 of the sampling tube 50.

The coal moves down the sampling tube 50 with a substantially zero pressure gradient or bulk density gradient in the manner to be described is analyzed by analyzer 92, and passes out through the oulet 56 to form a pile supported by the tray 90 under the upper rim of the discharge conveyor 80 and closing the outlet. The cleats 82 of the conveyor move to clear the pile by either returning the coal to the hopper 40 or discharging from the sampling apparatus.

Figure 5:
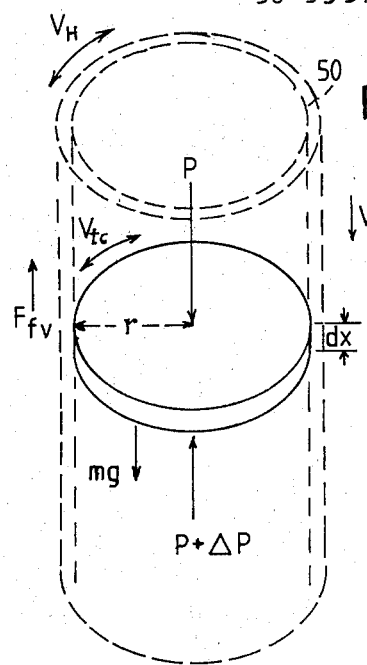
FIG. 5 is a schematic view of the forces applied to, and velocity of, an elemental disc of coal passing down the sampling tube of the apparatus.
Figure 6:
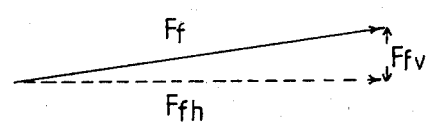
FIG. 6 is a vector diagram of the frictional forces on the elemental disc of FIG. 5.

Without wishing to be limited to any theoretical aspects underlining the present invention, the following discussin with reference to FIGS. 5 and 6 is given to explain how the coal passes down the tube under the influence of gravity, with no applied force, while maintaining a substantially zero pressure gradient or bulk density gradient.

Referring to FIGS. 5 and 6:
r = radius of the coal disc
dx = thickness of the coal disc
mg = weight of the coal disc
p = pressure on top of coal disc
P + ΔP = pressure on underside of coal disc
ΔP = pressure difference across coal disc
$V_v$ = vertical velocity of the coal disc
av = vertical acceleration of the coal disc
$V_{tc}$ = tangential velocity of the coal disc
$V_{tt}$ = tangential velocity of the tube
$F_f$ = total friction force
$F_{fv}$ = vertical vector component of the frictional force
$F_{fh}$ = horizontal vector component of the frictional force
μ = coefficient of friction.

Where the sampling tube 50 is stationary:
$V_{tt} = V_{tc} = 0'$
$F_{fv} = F_f = P.dx.2\pi r.\mu$ i.e. the frictional force between the coal and the interior surface of the tube is dependent on the pressure in the coal at any particular depth.

The mechanics of coal and other granular materials are such that any mechanism designed to push the coal from the inlet 49 of the tube to the outlet 56 leads to a very rapid increase in the force required to push the coal through the tube as the length-to-diameter ratio of the tube increases. This occurs because the force is required to overcome the friction between the coal and the wall of the tube throughout the entire length of the tube. Hence the applied force is rapidly dissipated as the frictional force between the wall and the coal increases, leading to an exponential increase in force as length, increases.

The invention uses the rotational or axial oscillation of the tube to exploit the fact that the inertia of the coal can be utilized to overcome the friction between the coal and the wall of the tube 50 so that the applied force is required only to cause the coal to move through the tube. Where the tube is substantially vertical (as hereinbefore described), gravitational forces are sufficient to move the coal through the tube without the need for any applied force.

In the preferred embodiment described, the tangential velocity of the tube ($V_{tt}$) is selected to be greater (preferably much greater) than the tangential velocity of the coal ($V_{tc}$), i.e.

$$V_{tt} >> V_{tc}$$

The frictional force in the vertical direction is markedly reduced and a horizontal vector component of the frictional force created so that the vertical component of the frictional force is less than the total frictional force i.e.

$$F_{fv} < F_f \text{ (see FIG. 6)}$$

By varying the tangential velocity of the tube ($V_{tt}$) and the amplitude of the oscillations, the vertical component of the frictional force ($F_{fv}$) can be selected to be equal to, or just less than, the weight of the coal, i.e.

$$F_{fv} \approx mg$$

Therefore no (or little) vertical acceleration force is applied to the coal disc, i.e.

$$a_v \approx 0$$

and the vertical velocity of the coal disc is substantially constant, i.e.

$$V_v \approx \text{constant}.$$

The pressure above the disc (P) is substantially equal to the pressure below the disc (P+ΔP), and so the pressure gradient across the disc is zero, i.e.

$$\Delta P = 0.$$

As the vertical vector component of the frictional force ($F_{fv}$) is not large, it cannot cause "hang-up" of the coal in the tube. The vertical velocity ($V_v$) of the coal will be determined by the rate of removal of the coal from the outlet 56 of the tube by the discharge conveyor 80.

The present invention has the further advantage that the small oscillation imparted to the coal by the tube causes the particles of coal to rearrange themselves within the columns of coal (particularly near the inlet 49 of the tube) so as to fill the voids which tend to occur in the columns. This achieves an essentially constant bulk density in the coal as it passes through the tube.

While the preferred embodiment has been described in relation to the sampling of coal, it is suitable for a wide range of granular materials where the same problems of passing the material through the tube arise.

As the discharge conveyor 80 will move a constant mass of granular material from the pile of granular material at the outlet 56 of the tube (the conveyor moves a constant volume of material in each revolution and the bulk density of the pile is constant), the method and apparatus hereinbefore described may be used as a constant mass flow feeder.

Various changes and modifications may be made to the embodiment described without departing from the scope of the invention defined in the appended claims. Throughout the description and claims, the word "tube" has been used to also include a "conduit".

We claim:

1. A method of conveying granular material through a sampling tube for analysis including the steps of:
   (a) feeding granular material to the sampling tube;
   (b) subjecting the sampling tube to oscillations to reduce the frictional force between the granular material and the wall of the sampling tube to enable the granular material to pass through the tube with substantially no pressure gradient or bulk density gradient, wherein the velocity and amplitude of the oscillations are selected such that the vertical vector component of the frictional force on an elemental disc of granular material in the bulk of the material is equal to or just less than the weight of the elemental disc so that the vertical velocity of the elemental disc is substantially constant; and (c) discharging the granular material from the sampling tube.

2. A method as claimed in claim 1, wherein in step (b), the sampling tube is subject to axial oscillations and/or rotational oscillations.

3. A method as claimed in claim 1 or claim 2 wherein in step (b), the velocity and/or amplitude of the oscillations are much greater than the velocity and/or amplitude or oscillation, respectively, of the granular material passing through the tube.

4. A method as claimed in claims 1 or 2 wherein in step (b), the sampling tube is substantially vertical and of substantially constant cross section, and the granular material passes down the sampling tube under gravitational force.

5. A method of conveying granular material through a sampling tube for analysis including the steps of:
(a) feeding granular material to the sampling tube;
(b) subjecting the sampling tube to oscillations to reduce the frictional force between the granular material and the wall of the sampling tube to enable the granular material to pass through the tube with substantially no pressure gradient or bulk density gradient, wherein the velocity and amplitude of the oscillations are selected such that the vertical vector component of the frictional force on an elemental disc of granular material in the bulk of the material is not greater than the weight of the elemental disc so that the vertical velocity of the elemental disc is substantially constant;
(c) analyzing the granular material as it passes through the sampling tube; and
(d) discharging the granular material from the sampling tube.

6. A method of conveying granular material as claimed in claim 1 or claim 2, further including the step of conveying the granular material discharged from the sampling tube at a constant volume flow rate.

7. Apparatus for conveying granular material through a sampling tube for analysis including:
a sampling tube having an inlet and an outlet;
means to support the sampling tube for oscillating movement;
means to feed granular material to the inlet of the sampling tube;
means for oscillating the sampling tube at a velocity and amplitude to reduce the frictional force between the granular material and the wall of the tube to enable the granular material to pass through the sampling tube with substantially no pressure gradient or bulk density gradient, said oscialiating means being such that the velocity and amplitude of the oscillations are selected so that the vertical vector component of the frictional force on an elemental disc of granular material in the bulk of the material is equal to or slightly less than the weight of the elemental disc so that the vertical velocity of the elemental disc is substantially constant; and
means for discharging the granular material from the outlet of the sampling tube.

8. Apparatus as claimed in claim 7 wherein:
the means for oscillating the sampling tube includes means to generate axial oscillations and/or rotational oscillations in the sampling tube.

9. Apparatus for conveying granular material through a sampling tube for analysis including:
a sampling tube having an inlet and an outlet;
means to support the sampling tube for oscillating movement;
means to feed granular material to the inlet of the sampling tube;
means for oscillating the sampling tube at a velocity and amplitude to reduce the frictional force between the granular material and the wall of the tube to enable the granular material to pass through the sampling tube with substantially no pressure gradient or bulk density gradient, said oscillating means being such that the velocity and amplitude of the oscillations are selected so that the vertical vector component of the frictional force on an elemental disc of granular material in the bulk of the material is not greater than the weight of the elemental disc so that the vertical velocity of the elemental disc is substantially constant;
means for discharging the granular material from the outlet of the sampling tube;
wherein:
the sampling tube is substantially vertical, of substantially constant cross-section, and is supported for rotational motion in a frame; and
the means for generating rotational oscillations in the sampling tube includes a substantially vertical drive shaft, at least one eccentric lobe on the drive shaft, a substantially vertical rocker shaft, at least one rocker arm on said rocker shaft; a drive link connecting the eccentric lobe to the rocker arm; diametrically opposed axles on the sampling tubes and a pair of connecting links connecting one of said axles to the adjacent end of the rocker arm, whereby the rotational motion of the drive shaft is translated into rotational oscillation of the sampling tube.

10. Apparatus as claimed in claims 7, 8, or 9 wherein the feeding means includes:
a hopper containing a supply of granular material;
a feed chute in communication with the inlet of the sampling tube; and
a bucket conveyor to convey granular material from the hopper to the feed chute.

11. Apparatus as claimed in claims 7, 8, or 9 wherein the discharge means includes:
a tray under the outlet of the sampling tube to support a pile of granular material discharged from the outlets; and
a reversible conveyor to convey granular material from the pile.

12. Apparatus as claimed in claims 7, 8, or 9 further including means to analyse the granular material in the sampling tube.

13. Apparatus as claimed in claim 11 wherein the reversible conveyor includes means for conveying the granular material from the pile at a constant volume flow.

* * * * *